M9

United States Patent
Hoffenblum

(10) Patent No.: US 9,456,982 B2
(45) Date of Patent: Oct. 4, 2016

(54) SOLID FORMULATIONS OF NIACIN TO COUNTERACT COLD EXTREMITIES

(71) Applicant: BE-WARM LLC, Troy, MI (US)

(72) Inventor: Harvey Hoffenblum, Troy, MI (US)

(73) Assignee: BE-WARM LLC, Troy, MI (US)

( * ) Notice: Subject to any disclaimer, the term of this patent is extended or adjusted under 35 U.S.C. 154(b) by 0 days.

(21) Appl. No.: 14/709,792

(22) Filed: May 12, 2015

(65) Prior Publication Data

US 2015/0328200 A1  Nov. 19, 2015

Related U.S. Application Data

(60) Provisional application No. 61/994,914, filed on May 18, 2014.

(51) Int. Cl.
*A61K 31/44* (2006.01)
*A61K 9/00* (2006.01)
*A61K 31/455* (2006.01)

(52) U.S. Cl.
CPC ........... *A61K 9/0056* (2013.01); *A61K 31/455* (2013.01)

(58) Field of Classification Search
None
See application file for complete search history.

(56) References Cited

U.S. PATENT DOCUMENTS

| | | |
|---|---|---|
| 4,466,958 A | 8/1984 | Morrison |
| 7,320,797 B2 | 1/2008 | Gupta |
| 7,666,451 B2 | 2/2010 | Mazzio et al. |
| 7,759,307 B2 | 7/2010 | Theoharides |
| 7,923,043 B2 | 4/2011 | Theoharides |
| 2003/0166614 A1 | 9/2003 | Harrison, Jr. |
| 2004/0081672 A1 | 4/2004 | Gupta |
| 2005/0048008 A1 | 3/2005 | Gupta |
| 2008/0050429 A1 | 2/2008 | Rocca et al. |
| 2009/0069275 A1 | 3/2009 | Rocca et al. |
| 2009/0148543 A1 | 6/2009 | Theoharides |
| 2010/0292280 A1 | 11/2010 | Zachar |
| 2011/0028548 A1 | 2/2011 | Fossel |
| 2012/0039957 A1* | 2/2012 | Brzeczko ............. A61K 9/2054 424/400 |

FOREIGN PATENT DOCUMENTS

| | | |
|---|---|---|
| CA | 2494743 | 7/2006 |
| CA | 2498639 | 9/2006 |
| CA | 2505808 | 11/2006 |
| WO | 2006052569 | 5/2006 |

* cited by examiner

*Primary Examiner* — Heidi Reese
(74) *Attorney, Agent, or Firm* — Technology Law PLLC; Karen L Kimble

(57) ABSTRACT

The present invention describes the use of niacin lozenges to warm the extremities of a human that is subjected to cold environments, such as working in cold conditions, outdoor sports, fans watching sports, and other such exposure to cold. The lozenges have 50 to 150 mg of niacin to cause the extremities of the human to warm but without the flushing result from higher doses of niacin.

13 Claims, No Drawings

SOLID FORMULATIONS OF NIACIN TO COUNTERACT COLD EXTREMITIES

FIELD OF THE INVENTION

The present invention concerns the preparation and use of a solid formulation containing niacin, vitamin B3, for use as a warming agent to mitigate human exposure to cold.

BACKGROUND OF THE INVENTION

Niacin is a vitamin known as vitamin B3 or nicotinic acid. Its chemical name is pyridine-3-carboxylic acid. It is an essential vitamin for human health.

Niacin doses for therapeutic uses are about 1.5 to 6 g/day. However, at these needed doses side effects are common such as dermatological conditions that often are displayed as skin flushing, itching, dry skin and skin rashes including eczema exacerbation and *Acanthuses nigricans*.

It has been thought that these symptoms are related to niacin's role as the rate limiting cofactor in the histidine decarboxylase enzyme, which converts 1-histidine into histamine. H1 and H2 receptor mediated histamine is metabolized via a sequence of mono- or di-amine oxidase and COMT into methyl histamine, which is then conjugated through the liver's CYP450 pathways. Persistent flushing and other symptoms may indicate deficiencies in one or more of the cofactors responsible for this enzymatic cascade.

Recently it has been thought that the flushing is primarily caused by prostaglandin ($PGD_2$), with serotonin appearing to have a secondary role in this reaction.

The actual mechanism of this superficial vasodilator flush syndrome (SVFS) in humans is not completely understood as yet.

Besides the SVFS side effect from these doses of niacin, additional side effects have been reported, for example gastrointestinal complaints, such as dyspepsia (indigestion), nausea and liver toxicity (fulminant hepatic failure). Additional side effects of hyperglycemia, cardiac arrhythmias, and "birth defects in experimental animals" have also been reported. [Keith Parker; Laurence Brunton; Goodman, Louis Sanford; Lazo, John S.; Gilman, Alfred (2006). *Goodman & Gilman's the pharmacological basis of therapeutics*. New York: McGraw-Hill.]

The SVFS flush lasts for about 15 to 30 minutes and sometimes longer, and is sometimes accompanied by a prickly or itching sensation, in particular, in areas covered by clothing. This has made the use of niacin therapy difficult for many persons and they cease its use.

Various attempts have been made to mediate this SVFS flushing and other skin reactions. A few of these attempts are discussed below.

Some attempts for modulation of the SVFS effect have combined niacin with various other compounds, for example: a flavonoid composition (U.S. Pat. No. 7,923,043, U.S. Pat. No. 7,759,307); making derivatives of niacin such as niacinamid or, nicotinic acid esters (US Appln. 2004/0081672, published Apr. 29, 2004); taking aspirin or ibuprofen (US Appln. 2010/0292280, published Nov. 18, 2010); consumption with food or as a food supplement with other ingredients such as fish oil concentrate and lecithin (US Appln. 2003/0166614, published Sep. 4, 2003) and phosphatidyl choline, phosphatidyl inositol and/or phosphatidyl ethanolamine, lecithin, a mucopolysaccharide, and silicon dioxide, silicic acid and/or organic esters of silicic acid (U.S. Pat. No. 4,466,958), and using a niacin receptor partial agonist and a lipid altering amount of niacin (WO 2006/052569, published May 18, 2006).

Using niacin in a topical application has been tried by many formulations such as for cosmetic uses in U.S. Pat. No. 7,320,797, for increasing local blood flow with L-arginine and theophylline in US Appln. 2011/0028548, published Feb. 3, 2011, for treating dyshidrosis and skin diseases in U.S. Pat. No. 7,666,451.

Additionally, forming sustained release formulations to lower the SVFS flushing effect have been tried when therapeutic doses of niacin are needed (CA Patent 2,505,808, CA Patent 2,498,639, and CA Patent 2,494,743). A matrix formulation has been tried for sustained release as tablets (US Appln. 2008/0050429, published Feb. 28, 2008, US Appln. 2009/0069275, published Mar. 12, 2009). However, these sustained release formulations where doses are above 2 g/day have been associated with liver damage. Extremely high doses of niacin can also cause niacin maculopathy, which is a thickening of the macula and retina, which leads to blurred vision and blindness. This maculopathy is often reversible after niacin intake ceases.

Besides being a vitamin that is usually in many multivitamin tables, many foods contain this vitamin.

Other known uses of niacin are to increase high-density lipoprotein (HDL), or the "good" cholesterol, as the HDL will aid the body on getting rid of low-density lipoprotein (LDL), or the "bad" cholesterol, in the bloodstream. Thus niacin may help boost the body's HDL levels. It is important to avoid too low an HDL level as that alone can still increase the risk of heart disease even if the LDL level and other factors are normal. [Mayo Clinic.com]

For all these uses of niacin, the SVFS flushing and skin reaction have been a deterrent to its use.

Clearly, a safe, reliable, pleasant niacin formulation for use as a warming agent for a person's extremities when exposed to cold weather with minimal or none of these side effects and that can be used repeatedly over long periods of time is needed.

BRIEF SUMMARY OF THE INVENTION

The present invention is the use of niacin lozenges to treat cold extremities of humans without the SVFS flushing result. Humans exposed to cold conditions have needed to keep their hands and toes warm and avoid frost nip and frost bite. The present invention provides a formulation for the use of a low dose of niacin to cause the desired warming effect in these extremities while avoiding or minimizing the flushing or skin itching side effect. This use is also an object of this invention.

A formulation and method for its use in warming the extremities of a human subjected to cold conditions, said method comprising administering one or more lozenges of a solid formulation to said human comprising:
 a) Niacin at about 50 mg to about 150 mg or about 4% to about 12% w/w of the total lozenge;
 b) One or more low calorie sweeteners of about 0.05% to about 1% w/w of the total lozenge;
 c) One or more pharmaceutically-acceptable additives of about 85% to about 95.95% w/w of the total lozenge; and
 d) Optional flavoring of about 1% to about 2% w/w of the total lozenge.

The lozenges are prepared from the above formulation by using conventional or high shear mixing of the niacin and sweetener ingredients and enough water to provide through blending. The final mixture is dried to form granules and then mixed with the remaining ingredients and pressed into the lozenges each containing about 50 to about 150 mg of niacin. Thus the process comprises:

a) Adding the pharmaceutically-acceptable additives to a blender;
b) Adding the niacin in distilled water to the blender and mixing until homogenous; and
c) Adding the low calorie sweetener and mixing; and
d) Adding the flavoring agent desired and mixing; and
e) Drying to form granules; and
f) Pressing the paste or powder in a high pressure pharmaceutically-acceptable press to form the lozenge, and
g) Packaging.

Alternatively, the mixture has some water present and is pressed into the lozenge and then dried. The formulation does not require a release retarding agent or other sustained release additive. This formulation releases niacin over about 15 to 30 minutes after oral administration.

DETAILED DESCRIPTION OF THE INVENTION

In persons who are not accustom to exposure to cold weather, when they are exposed to such cold conditions, their bodies immediately respond to a drop in ambient temperature by exhibiting an immediate vasoconstriction such that their extremities in their fingers and toes are cold. Even after the initial response to the cold exposure and the body's thermostat is on "high", this vasoconstriction continues. In contrast, a person who is acclimated to the cold has limited or no such vasoconstriction reaction.

By this vasoconstriction reaction the body is decreasing the peripheral blood flow that reduces convective heat transfer between the body's core (internal body temperature) and the skin (including subcutaneous fat and skeletal muscle). This response by the body effectively insulates the internal body temperature from the cold.

Heat is lost from the skin on an exposed body surface faster than it is replaced (less blood flow) causing the skin and underlying body tissue temperatures to decline. Thus on the exposure to cold, the vasoconstrictor response helps retain the internal body temperature and retard the loss of heat, but at the expense of a decline in skin and muscle temperature. This can lead to peripheral cold injuries effecting the hands, fingers and toes, making them susceptible to cold injury such as frost nip and frost bite.

The use of niacin to blunt or reverse the vasoconstriction response to cold can be accomplished if its dose can be selected to cause vasodilation but avoid the flushing response experienced from large niacin doses.

Accomplishing this result provided by the present invention has proven difficult as niacin has a wide therapeutic dosing range (e.g., about 1 to 2 g per day as seen from all its various therapeutic uses discussed above) but has a narrow therapeutic index.

For the purpose of this invention the formulation is taking advantage of the very wide dosing range to attain the warming effect of niacin for use by a person to attain the desired warming effect of the skin, fingers and toes. The variables that affect the dose are body mass, body type, age and gender of the person. Thus the person must decide when the dose is enough to obtain the desired warmth. If this dose is exceeded, the flushing effect can occur. Thus each person must determine how many lozenges to take to get the warming effect desired.

One purpose is to get the skin warm, but without getting the undesired flushing effect, by moderation of the dose of niacin. Because of this difficulty of so many variables in the dose determination, few studies have been done.

When high doses of niacin are administered for therapeutic purposes such as discussed above, the various mitigated efforts are made to lesson or stop this flushing effect. This entails more management of the side-effect.

A purpose of this invention is to provide a dose of niacin that will provide the warming effect without the flushing effect, while yet being flexible enough to deliver a wide range of doses with a consistent niacin level over the desired time.

Niacin is a water-soluble, active ingredient in the present formulation. It is commercially available as fine white crystals, granules or white crystalline powder. Although all these forms can be used in the present formulation, the preferred form for the present composition is using the granular form as it has better handling characteristics for making the present lozenges. The present lozenge has from about 50 to about 150 mg of niacin. This dose is well below the therapeutic doses discussed above and does not cause flushing. This amount of niacin is about 4 to about 12% w/w in the lozenge.

There is no required sustained release agent present as this lozenge (buccal tablet) releases niacin over about a 15 to 30 minute period. The compression of the buccal tablet is very high so that the tablet disintegrates at a very slow rate in the oral cavity (taken by mouth). This rate of release avoids a bolus dosing and minimizes any flushing effect.

Because this lozenge is oral and dissolves in the mouth, it should be pleasant tasting. Therefore, low calorie sweeteners and flavorings as desired are used in the lozenge. Low calorie sweeteners are aspartame, xylitol, sucralose, sorbitol and/or Splenda® (trademark of McNeil Nutritionals, LLC) which is a sucralose-based artificial sweetener derived from sugar, blended with maltodextrin. Xylitol is a low caloric naturally occurring sweetener used in chewing gums. Xylitol is classified as a GRAS substance and imparts a pleasant taste. Splenda and aspartame are well-known artificial sweeteners. The sweetener added to the lozenge may be one or more of these sweeteners. The total amount of sweetener in each lozenge is 0.05% to about 1% w/w (w/w means weight by weight).

Some flavorings, especially natural flavors, but also artificial flavors, may be added as desired to the lozenge, and include spearmint, wintergreen, peppermint, orange, cherry, strawberry, peach, grape, mixed berry or other suitable flavors. This amount of flavoring is from 1% to about 2% w/w of the total lozenge.

One or more of pharmaceutically-acceptable additives such as excipients and carriers are present that enable the lozenge to be pressed into the desired dose and size. One of these additives is a lubricant such as talc, magnesium stearate, calcium stearate, stearic acid, hydrogenated vegetable oils, and the like. Maltodextran is added as an excipient that is also a sweetener. Fillers such as microcrystalline cellulose and binders such as polyvinyl alcohol can be added. Other additives are binders, lubricants, wetting agents, fillers, excipients, buffers (acid or base), preservatives, stabilizers, and any other additives that are known from readily available sources such as *Handbook of Pharmaceutical Excipients*. All ingredients are pharmaceutically-acceptable or food grade approved for human consumption.

The relative amounts of ingredients in one lozenge can vary over a wide range from about 85% to about 95.95% w/w of the total lozenge so long as the amount of niacin is between about 50 to about 150 mg and is about 4 to about 12% w/w in the lozenge.

The number of lozenges consumed at a time and the timing for repeating of the dose—as needed to continue the warming response—can be determined by the individual very easily. The person starts with the lowest recommended dose—1 lozenge of about 50 to about 100 mg of niacin—and after about 30 minutes determines if he/she is "warm". The niacin in the formulation releases over about 15 minutes. If yes, no more is taken until they begin to feel cold and another lozenge is then taken. If they do not feel warm, another lozenge is taken and another 30 minutes to wait to see if they are "warm". Once a person knows how many lozenges they need, they can consume that number when they feel cold. Because of the undesired flushing effect by taking too high a dose, a person will want to take the lowest dose they can or if this flushing happens they will know to take less. Thus very quickly a person will know the correct dose for them. For example, an experiment was done to test both the lozenge and the dose where 80 college male skiers of ages 18-22 were testing these lozenges and the average dose was 75 mg of niacin to feel "warm"; thus some persons needed 50 mg while others needed 150 mg (1 to 2 lozenges) but they were able to regulate this dose easily.

The lozenges are in a convenient package so that they can be carried on the person to take when they experience cold or just before they are going out into the cold. No food is required as with some prior doses of niacin. No other mediator product is needed. Thus these lozenges of this invention are very easy to carry in a pocket and use when needed.

The persons that will benefit from this product are those who play winter sports, outdoor sports fans, those who enjoy outdoor activities, and also for those persons exposed in their work and/or activities to possible frost nip or frost bite.

Each present lozenge formulation comprises:
 a) Niacin at about 50 mg to about 150 mg or about 4% to about 12% w/w of the total lozenge;
 b) One or more low calorie sweeteners of about 0.05% to about 1% w/w of the total lozenge;
 c) One or more pharmaceutically-acceptable additives of about 85% to about 95.95% w/w of the total lozenge; and
 d) Optional flavoring of about 1% to about 2% w/w of the total lozenge.

The total lozenge weight is about 1.0 to 1.5 g, and is a hard tablet that is compressed at high pressure. These lozenges have an estimated shelf life of about 2 years.

The present formulation is prepared by:
 a) Adding the pharmaceutically-acceptable additives to a blender;
 b) Adding the niacin in distilled water to the blender and mixing until homogenous; and
 c) Adding the low calorie sweetener and mixing; and
 d) Adding the flavoring agent when desired and mixing; and
 e) Drying to form granules; and
 f) Pressing the paste or powder in a high pressure pharmaceutically-acceptable press to form the lozenge as a hard tablet, and
 g) Packaging.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. All such modifications that fall within the spirit and broad scope of the appended claims are included.

What is claimed is:

1. A method of warming the extremities of a human subjected to cold conditions, said method comprising administering one or more lozenges of a solid formulation to said human comprising:
 a) Niacin at about 50 mg to about 150 mg or about 4% to about 12% w/w of the total lozenge;
 b) One or more low calorie sweeteners of about 0.05% to about 1% w/w of the total lozenge;
 c) One or more pharmaceutically-acceptable additives of about 85% to about 95.95% w/w of the total lozenge; and
 d) Optional flavoring of about 1% to about 2% w/w of the total lozenge.

2. The method of claim 1, wherein the pharmaceutically-acceptable additive comprises one or more additional ingredients selected from binders, lubricants, wetting agents, fillers, excipients, buffers, preservatives, stabilizers, desiccants and any other pharmaceutically-acceptable additives.

3. The method of claim 2, wherein the lubricant is talc, magnesium stearate, calcium stearate, stearic acid, or hydrogenated vegetable oils.

4. The method of claim 1, wherein the low calorie sweetener is aspartame, xylitol, sucralose, sorbitol, and/or maltodextrin.

5. The method of claim 1, wherein the flavoring is spearmint, wintergreen, peppermint, orange, cherry, strawberry, peach, grape, mixed berry or other suitable flavors.

6. The method of claim 1, wherein the formulation is administered to a human in an amount from 1 lozenge to 2 lozenges at one time for use as a warming agent.

7. The method of claim 6, wherein multiple doses are taken over time by the human as needed for use as a warming agent.

8. The method of claim 1, where the lozenge releases the niacin over about 15 to 30 minutes on oral consumption.

9. A solid lozenge containing niacin as the active ingredient in about 50 to 150 mg per lozenge with the remainder of the lozenge being flavoring agents, low calorie sweeteners, and one or more pharmaceutically-acceptable additives.

10. The lozenge of claim 9, wherein e lozenge has a weight from about 1.0 to 1.5 g and is a hard compressed tablet.

11. The lozenge of claim 9 wherein the pharmaceutically-acceptable additives are one or more additional ingredients selected from hinders, lubricants, wetting agents, fillers, excipients, buffers, preservatives, stabilizers, desiccants and any other pharmaceutically-acceptable additives.

12. The lozenge of claim 11 wherein the lubricant is talc, magnesium stearate, calcium stearate, stearic acid, or hydrogenated vegetable oils.

13. The lozenge of claim 9 wherein the low calorie sweetener is aspartame, xylitol, sucralose, sorbitol, and/or maltodextrin.

* * * * *